United States Patent
Lomel et al.

(10) Patent No.: US 8,802,810 B2
(45) Date of Patent: Aug. 12, 2014

(54) PROCESS FOR THE MANUFACTURE OF A SOLUTION OF SALTS OF DIACIDS/DIAMINE(S)

(75) Inventors: Sébastien Lomel, Saint Just Chaleyssin (FR); Jean-Francois Thierry, Francheville (FR); Véronique Bossennec, Serezin-du-Rhône (FR)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 13/260,266

(22) PCT Filed: Mar. 25, 2010

(86) PCT No.: PCT/EP2010/053946
§ 371 (c)(1),
(2), (4) Date: Nov. 3, 2011

(87) PCT Pub. No.: WO2010/115727
PCT Pub. Date: Oct. 14, 2010

(65) Prior Publication Data
US 2012/0046439 A1 Feb. 23, 2012

(30) Foreign Application Priority Data
Apr. 9, 2009 (FR) .................................... 09 52333

(51) Int. Cl.
*C08G 69/28* (2006.01)
*C07C 51/41* (2006.01)

(52) U.S. Cl.
CPC ................ *C08G 69/28* (2013.01); *C07C 51/41* (2013.01)
USPC ................ 528/336; 528/351; 556/6

(58) Field of Classification Search
CPC ................ C08G 69/28; C07C 51/41
USPC .................. 524/845; 528/336, 351; 556/6
See application file for complete search history.

(56) References Cited

U.S. PATENT DOCUMENTS

| | | | |
|---|---|---|---|
| 4,118,351 A * | 10/1978 | Murray et al. | 528/324 |
| 5,028,462 A * | 7/1991 | Matlack et al. | 428/35.7 |
| 5,891,987 A * | 4/1999 | Yuo et al. | 528/338 |
| 6,284,830 B1 * | 9/2001 | Gottschalk et al. | 524/449 |

FOREIGN PATENT DOCUMENTS

| | | |
|---|---|---|
| EP | 0 812 869 A2 | 12/1997 |
| EP | 812869 A2 * | 12/1997 |
| GB | 830 676 A | 3/1960 |
| GB | 830676 B * | 3/1960 |
| JP | 59-187024 | 10/1984 |
| JP | 2008-239908 A | 10/2008 |
| JP | 2008239908 A * | 10/2008 |

* cited by examiner

*Primary Examiner* — Kelechi Egwim
(74) *Attorney, Agent, or Firm* — Dentons US LLP

(57) ABSTRACT

A method for manufacturing a solution of a diacid and diamine salt for manufacturing polyamide is described. A method for manufacturing an aqueous solution of diacid and diamine salts produced by mixing at least two diacids and at least one diamine, with a weight concentration of salt between 40% and 70%, including, in a first step, preparing an aqueous solution of diacid(s) and diamine(s) with a diacid/diamine mole ratio of less than 1 using one diacid and one diamine, and in a second step, adjusting the mole ratio of diacids/diamine(s) to a value of between 0.9 and 1.1, and fixing the weight concentration of salt by adding another diacid and, optionally, additional water and/or diamine is also described.

13 Claims, 2 Drawing Sheets

PROCESS FOR THE MANUFACTURE OF A SOLUTION OF SALTS OF DIACIDS/DIAMINE(S)

Figure 1:
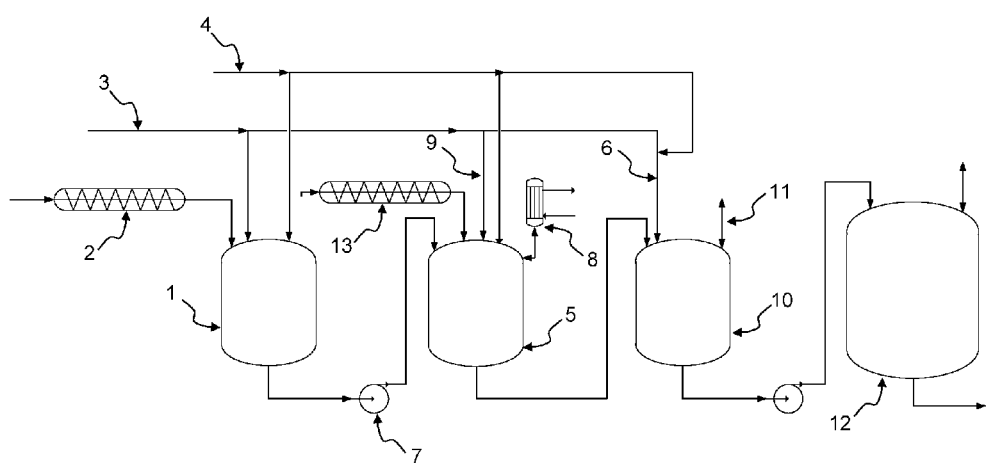

This application is the United States national phase of PCT/EP2010/053946, filed Mar. 25, 2010, and designating the United States (published in the French language on Oct. 14, 2010, as WO 2010/115727 A1; the title and abstract were also published in English), and claims foreign priority under 35 U.S.C. §119 of FR 0952333, filed Apr. 9, 2009, each hereby expressly incorporated by reference in its entirety and each assigned to the assignee hereof.

The present invention relates to a process for the manufacture of a solution of a salt of diamine(s) and of diacids for the manufacture of polyamide.

Use is generally made, in order to obtain polyamides comprising diacid and diamine monomers of high molecular weight, of an aqueous solution of a salt formed by reaction between one molecule of diamine and one molecule of diacid. This solution is heated in order to evaporate the water, in a first step, and then in order to start the polymerisation by polycondensation, in order to obtain macromolecular chains comprising amide functional groups.

The salt solution generally comprises essentially stoichiometric amounts of diacid(s) and diamine(s). The concentration by weight of Nylon salt (hexamethylenediammonium adipate salt) used as starting material for the manufacture of polyamide, more specifically of PA66, is generally between 50% and 65%. This solution is generally stored before being transported, if appropriate, and then fed in polymerisation plants.

Several processes for the manufacture of a solution of salt of diacid(s) and of diamine(s) have been provided. For the manufacture of Nylon salt, these processes generally consist in adding the adipic acid to hexamethylenediamine, or vice versa, in the aqueous medium, while removing or not removing the heat produced by the neutralisation reaction.

A number of monomers of different natures are employed in the manufacture of copolyamides, in particular of copolyamides starting from aromatic diacids, from adipic acid and from hexamethylenediamine. Problems of dissolution of these different monomers are encountered upstream of the reaction for the polymerisation of these copolyamides, during the preparation of the solution of salt of diacids and of diamine(s) starting from these different monomers. For example, dissolution is sometimes impossible, or the dissolution time is very long, or it is necessary to employ very dilute solutions. This can cause problems of productive output, of quality of the product, of storage and transportation of the solution in the polymerisation plant.

A search is thus underway for processes for the preparation of a solution of acids and of diamine(s) not exhibiting these problems.

To this end, the invention provides a process for the manufacture of an aqueous solution (A) of salts of diacids and diamine(s) which are obtained by mixing at least two diacids and at least one diamine at a concentration by weight of salt of between 40 and 70%, characterized in that it comprises the following stages:

producing, in a reactor, an aqueous solution (A') of diamine(s) and diacid(s) having a diacid/diamine molar ratio of less than 1, preferably of less than or equal to 0.9, by feeding, to the said reactor comprising a liquid at a temperature of between 55 and 95° C. (limits included), preferably between 60 and 90° C. (limits included), comprising water and diamine, a stream (B') comprising a diacid, optionally a stream comprising diamine and optionally a stream comprising water; the flow rates of the feed stream or streams being controlled in order to always have a temperature of the solution in the reactor which is less than the boiling point of the solution under the operating pressure; the amounts of water and of diamine in the liquid and the flow rates of the feed streams being controlled in order to always have a diacid(s)/diamine(s) molar ratio of less than 1; the diacid of the stream (B') being an aliphatic or cycloaliphatic diacid comprising a number of carbon atoms of greater than 10 or an aromatic diacid;

mixing the aqueous solution (A') resulting from the first stage with a stream (B") comprising at least one diacid, the diacid being an aliphatic or cycloaliphatic diacid comprising a number of carbon atoms of less than or equal to 10, and optionally supplementary water and/or supplementary diamine; in order to obtain an aqueous solution (resulting from the mixing of (A') and (B")) having a diacids/diamine(s) molar ratio of between 0.9 and 1.1, preferably between 0.98 and 1.02 (limits included); this solution being brought to a temperature at most equal to the boiling point of the solution at the operating pressure by at least the release of heat of the reaction between the diamine(s) and the diacids; in order to obtain the solution (A) of diacids and diamine(s) at the desired concentration and the desired composition.

The term "boiling point" should be understood as meaning the boiling point of the solution present in a reactor at the working or operating pressure of the process.

Mention may be made, as diamines suitable for the invention, of hexamethylenediamine (HMD) as preferred and most widely used monomer and also heptamethylenediamine, tetramethylenediamine, octamethylenediamine, nonamethylenediamine, decamethylenediamine, 2-methyl-pentamethylenediamine, undecamethylenediamine, dodecamethylenediamine, xylylenediamine, or isophoronediamine. It is possible to use a mixture of several diamine monomers.

In the process of the invention, the diamine can be employed in the pure form or in the form of a concentrated aqueous solution. For HMD, a solution comprising at least 50% by weight of diamine, preferably at least 85% and more advantageously still 90% by weight approximately, can be used. However, the streams comprising the diamine can comprise other compounds without, however, departing from the scope of the invention.

Mention may be made, as aromatic diacid or aliphatic or cycloaliphatic diacid comprising a number of carbon atoms of greater than 10 suitable for the invention, of dodecanedioic acid, isophthalic acid, terephthalic acid or naphthalenedicarboxylic acid, for example. The preferred diacid is terephthalic acid.

Mention may be made, as aliphatic or cycloaliphatic diacid comprising a number of carbon atoms of less than or equal to 10 suitable for the invention, of adipic acid, suberic acid, sebacic acid, azelaic acid, pimelic acid or cyclohexanedicarboxylic acid. The preferred diacid is adipic acid.

The diacids are generally used in the powder form. However, they can also be in the form of an aqueous solution or of a suspension.

Advantageously, use is made of a mixture of aromatic diacid and of aliphatic diacid. The molar proportion of aromatic diacid with respect to the aliphatic diacid is between 5 and 80%, preferably between 20 and 50%. Preferably, the aromatic diacid is terephthalic acid and the aliphatic diacid is adipic acid. Advantageously, the molar proportion of terephthalic acid with respect to the diacids is between 5 and 80%, preferably between 20 and 50%.

As for the streams comprising the diamine, the streams comprising the diacid can comprise other compounds, such as solvents, without, however, departing from the scope of the invention.

Chain limiters can be introduced during the implementation of the process of the invention, for example during the first stage of the process for the preparation of the aqueous solution (A') or in the stream (B"). Mention may be made, as an example of chain limiters, for example, of benzoic acid, acetic acid and the like.

The first stage of the process of the invention consists in preparing an aqueous solution (A') of diamine(s) and diacid(s) having a diacid/diamine molar ratio of less than 1, preferably of less than or equal to 0.9.

The preparation of this aqueous solution (A') consists in feeding, to a liquid comprising water and diamine, a stream (B') comprising the diacid. Advantageously, the water and the diamine of the liquid represent all the water and diamine of the solution (A'). When the water and the diamine of the liquid do not represent all the diamine and water of the liquid, a stream of diamine and/or a stream of water can also be fed to the reactor, in addition to the stream (B') comprising the diacid. The diamine of the liquid (A') is advantageously hexamethylenediamine.

The concentration of water in the liquid can vary within a wide range. However, the concentration is sufficiently high to allow the dissolution of the diacid of the stream (B') and thus the acquisition of the solution (A') within a reasonable period of time. Advantageously, the concentration of water in the liquid is greater than or equal to 30% by weight.

The liquid is at a temperature of between 55 and 95° C. (limits included), preferably between 60 and 90° C. (limits included). This makes it possible to be positioned under the best conditions for carrying out the dissolution of the diacid of the stream (B'). The liquid may or may not be heated.

The liquid can also comprise a portion of the aliphatic or cycloaliphatic diacid having a number of carbon atoms of less than or equal to 10, corresponding or not corresponding to the diacid introduced in the stream (B").

According to a specific embodiment of the process of the invention and when the process is a batchwise process, the reactor, at the beginning of the first stage of the process, can comprise a small amount of aqueous solution (A) or of aqueous solution (A'), known as solution heel. This aqueous solution is a small portion of the solution (A) or of the solution (A') prepared in a previous operation.

The amount of such a solution (A) or solution (A') present in the reactor at the beginning of the first stage is equal to at least approximately 5% by weight, advantageously between 5 and 40% by weight, preferably between 10 and 35% by weight, of the total amount of the solution (A) or of the solution (A') to be produced in the reactor.

Advantageously, according to a characteristic of the invention, the heat exchanges between the reactor and the environment, or the outside, are minimised, that is to say that the reactor operates in quasiadiabatic mode.

The temperature in the reactor during the feeding of the stream (B') can rise because of the neutralisation reaction between the diamine and the diacid. However, the temperature of the solution in the reactor, throughout the operation and at the end of the stage, will always be less than the boiling point of the solution under the operating pressure.

The diacid of the stream (B') is an aromatic diacid or an aliphatic or cycloaliphatic diacid comprising more than 10 carbon atoms. It is advantageously terephthalic acid.

The concentration of water in the solution (A') can vary within a wide range, according to the desired concentration of the final salt and thus according to the amount of water optionally contributed by the stream (B").

According to a specific embodiment of the process of the invention, the temperature of the solution (A') is greater than or equal to 75° C., in order to prevent any appearance of solid phase in the solution (A').

The implementation of the first stage of the process of the invention makes it possible to produce very good dissolution of the diacid of the stream (B').

In a second stage of the process of the invention, the solution (A') resulting from the first stage is mixed with a stream (B") comprising at least diacid and optionally supplementary water and/or supplementary diamine. This makes it possible to obtain an aqueous solution (resulting from a mixing of (A') and (B")) having a diacids/diamine(s) molar ratio of between 0.9 and 1.1, preferably of between 0.98 and 1.02 (limits included). This stage makes it possible to obtain a solution of diacids and diamines at the desired concentration and the desired composition.

Water can also be added in order to adjust the concentration of salt of diacid(s)/diamine(s) to a concentration by weight of greater than 40%, preferably of between 50 and 65%. The water can advantageously be mixed with the stream of acid.

The diacid of the stream (B") is an aliphatic or cycloaliphatic diacid comprising a number of carbon atoms of less than or equal to 10. It is advantageously adipic acid.

Advantageously, the stream (B") is an aqueous solution of diacid and of diamine with a diacid/diamine molar ratio of between 1.5 and 5 and a concentration in the water of the dissolved entities of between 40 and 75%, preferably between 45 and 65%. The diamine of the stream (B") is advantageously hexamethylenediamine. The temperature of the stream (B") is sufficiently high to prevent any appearance of solid phase in the stream (B"). The heat of the neutralisation reaction of the amine by the acid brings about an increase in the temperature in the reactor for the preparation of the stream (B"), to reach at the most the boiling point of the mixture at the operating pressure.

The term "dissolved entities" should be understood as meaning all of the diacid and diamine entities present in the medium in the free form, in the ionic (salt) form or in another form.

According to a specific embodiment of the process of the invention and when the process is a batchwise process, the reactor for the preparation of the stream (B") can, at the beginning of the preparation of the stream (B"), comprise a small amount of stream (B"), known as heel. This heel is a small portion of the stream (B") prepared in a previous operation.

The amount of such a heel present in the reactor at the beginning of the preparation of the stream (B") is equal to at least approximately 5% by weight, advantageously between 5 and 40% by weight, preferably between 10 and 35% by weight, of the total amount of stream (B") to be produced in the reactor.

Advantageously, according to a characteristic of the invention, the heat exchanges between the reactor and the environment, or the outside, are minimised, that is to say that the reactor operates in quasiadiabatic mode.

According to a specific embodiment of the process of the invention, the process of the invention comprises an additional stage of adjusting the diacids/diamine molar ratio, for example to a value of between 0.995 and 1.005. This stage is preferably carried out by addition of diamine and of water.

The process of the invention is advantageously carried out while maintaining the reactor(s) under an oxygen-free atmosphere, such as, for example, under an atmosphere composed of nitrogen, rare gases, water vapour or a mixture of these.

In a preferred embodiment, the oxygen-free atmosphere is obtained either, on the one hand, by continuously feeding a stream of nitrogen or, on the other hand, by maintaining a pressure of nitrogen in the reactor(s) and by generating steam by boiling the solution.

In the latter case it is advantageous for the escape or discharge of the nitrogen to be carried out through a condenser fitted to the reactor(s). Thus, the water entrained with the nitrogen is condensed and recycled to a reactor(s).

This embodiment also makes possible the discharge of the oxygen present, for example in dissolved form, in the solution and thus prevents oxidation of the monomers, in particular of the diamine. The oxygen can be introduced in particular by the diacid monomers.

According to another embodiment, the reactor is kept under an oxygen-free atmosphere by feeding, for example, nitrogen into the empty reactor and maintaining this nitrogen atmosphere during the operations for filling and emptying the reactor.

In this embodiment, the dissolved oxygen will be discharged by entertainment by the nitrogen which escapes from the reactor during the filling of the latter. This discharge of the nitrogen is carried out, preferably, through a condenser in order thus to condense the water vapour entrained by the nitrogen.

Preferably, the reactor(s) is (are) provided with thermal insulation in order to limit heat exchanges with the external environment and thus to limit heat losses.

The process of the invention can be carried out according to a batchwise mode or a continuous mode. These two embodiments are described in detail below.

The process of the invention can be carried out in any type of reactor. More particularly, the reactors into which solid material is introduced comprise mechanical stirring and can be equipped with means which make it possible to maintain the temperature thereof, in particular during periods of shutdown or of change in manufacturing campaign. Use may be made, in order to obtain homogenisation of the solution in the reactor, of an external circulation loop comprising a pump.

The process of the invention can be carried out in a single reactor or in several reactors. These reactors can, for example, be connected in parallel or in series.

According to the process of the invention, the diacids/diamine molar ratio can advantageously be controlled and adjusted by the measurement of the pH of the solution and the addition of supplementary diacid and/or diamine according to the result of this pH measurement.

The salt solution obtained according to the process of the invention can be fed directly to a polymerisation plant or can be stored in a storage tank or in containers suitable for transportation, before optionally transfer and use.

Figure 2:
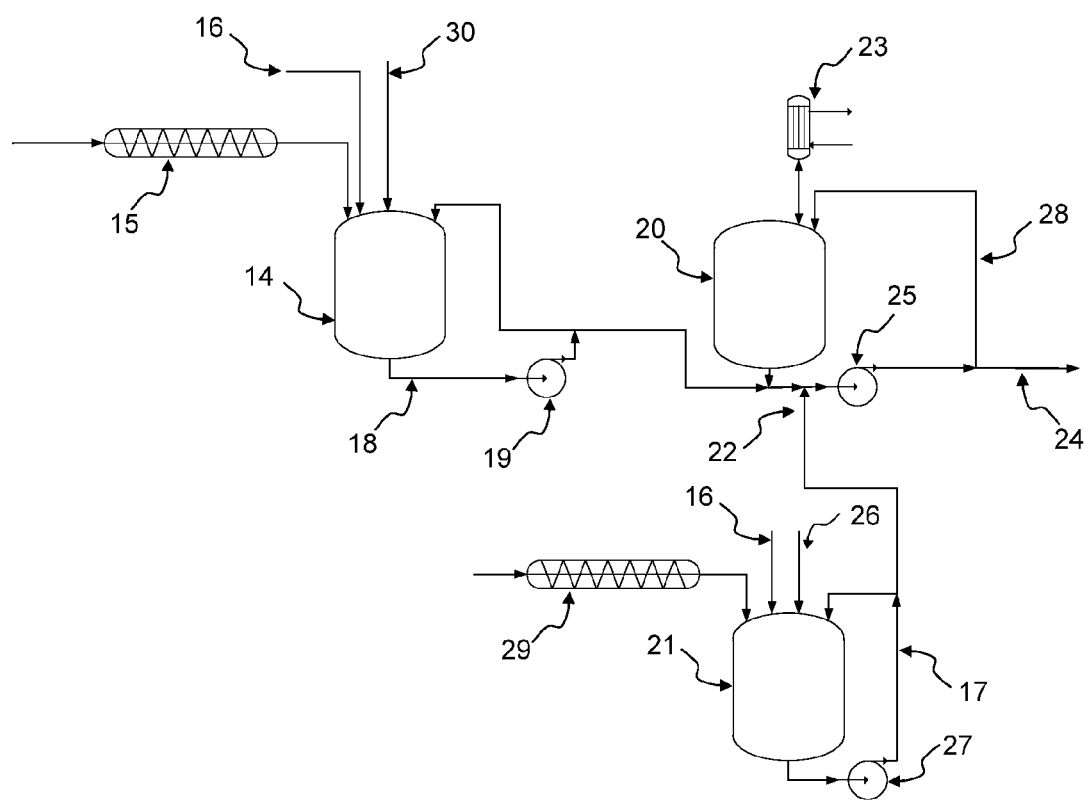

A detailed description of two embodiments of the process of the invention is given below, with reference to the appended FIGS. 1 and 2, in which:

FIG. 1 represents a block diagram of a plant which makes it possible to implement the process according to a batchwise embodiment, and FIG. 2 represents a block diagram of a plant which makes it possible to implement the process according to a continuous embodiment.

The invention is also illustrated by the examples of the manufacture of salt solutions obtained according to the batchwise embodiment of the process.

In the description below, the terms adipic acid (AA), terephthalic acid (TA) and hexamethylenediamine (HMD) will be used to denote the diacids and the diamine. However, this process also applies to other diacids and other diamines indicated above.

A first embodiment of the process of the invention operating according to the batchwise mode is described with reference to FIG. 1. The plant comprises a first stirred reactor 1, to which adipic acid 2, generally in the form of a powder, and a liquid stream 3 of hexamethylenediamine are added. Water 4 is also introduced into this reactor.

The various products are added to reactor 1, which comprises a small amount of solution of adipic acid and of hexamethylenediamine in water which is rich in adipic acid and is known as solution heel. This aqueous solution is advantageously a small portion of the solution prepared in a previous operation and advantageously has, as composition, substantially the final composition of the solution which will be prepared in this reactor 1, namely a diacid/diamine molar ratio equal to approximately 2.4 and a concentration by weight of dissolved entities of approximately 57%.

The plant also comprises a second stirred reactor 5 to which water 4, a liquid stream 9 of hexamethylenediamine and terephthalic acid 13, generally in the powder form, are added.

The hexamethylenediamine and the water are added to the reactor 5, which comprises a small amount of solution of terephthalic acid, of adipic acid and of hexamethylenediamine in water, known as solution heel. This aqueous solution is advantageously a small portion of the solution (A) prepared in a previous operation and advantageously has, as composition, substantially the final composition of the solution (A) which will be prepared in this reactor 5, namely a diacid/diamine molar ratio equal to approximately 1.017 and a concentration by weight of dissolved entities of approximately 52%. The terephthalic acid is subsequently introduced into the reactor 5. The complete dissolution of the terephthalic acid is obtained.

The solution of the reactor 1 is subsequently fed to the second reactor 5 via a pump 7. This reactor 5 is equipped with a condenser 8 and advantageously with an external loop for circulating the solution and/or with a stirrer (not represented).

The solution of the reactor 1 is fed to this reactor 5 in order to obtain a diacid/HMD molar ratio in the vicinity of 1.017. As for the first reactor 1, no significant heat exchange is advantageously produced with the exterior. Thus, the heat of the neutralisation reaction of the amine by the acid brings about an increase in the temperature in the reactor 5 to reach at the most the boiling point of the mixture at the operating pressure. The water which evaporates is condensed in the condenser 8 to obtain total reflux of the water.

In the mode illustrated, which is the preferred mode of the invention, the solution obtained in the second reactor 5 is fed to a third reactor 10 equipped with a homogenisation means (not represented) and optionally with a condenser 11.

This third reactor 10, also known as adjustment reactor, comprises an addition 6 of HMD and of water in order to adjust the diacids/HMD ratio to a value, for example, of between 0.995 and 1.005 and to adjust, if necessary, the concentration of salt to the desired value.

The solution thus obtained can be used directly in a polymerisation plant or can be stored in a storage tank 12 or in containers suitable for transportation.

A second embodiment of the process of the invention is described with reference to FIG. 2. This second embodiment relates to a process operating according to a continuous mode. As in the first embodiment, the process comprises a first stage of dissolution of the adipic acid carried out in the reactor 14.

The adipic acid is fed via an endless screw system 15, simultaneously with water 16 and with diamine 30 in the pure or aqueous solution form, to obtain, in the reactor 14, a solution comprising a diacid/diamine molar ratio of between 1.5 and 5, preferably in the vicinity of 2.4, and a concentration by weight of dissolved entities of between 40 and 75%, for example equal to 57%.

An external circulation loop 18 comprising a pump 19 in order to obtain homogenisation of the solution in the reactor 14 is illustrated. The reactor 14 is also equipped with a mechanical stirrer (not represented). A portion of the solution circulating in the loop feeds a reactor 20.

As in the first embodiment, the process comprises a stage of dissolution of the terephthalic acid carried out in the reactor 21. The terephthalic acid is fed via an endless screw system 29, simultaneously with water 16 and with diamine 26 in the pure or aqueous solution form, to obtain, in the reactor 21, a solution comprising a diacid/diamine molar ratio less than 1, for example in the vicinity of 0.48, and a concentration by weight of dissolved entities, for example, equal to 49%.

An external circulation loop 17 comprising a pump 27 in order to obtain homogenisation of the solution in the reactor 21 is illustrated. The reactor 21 is also equipped with a mechanical stirrer (not represented). A portion 22 of the solution circulating in the loop feeds a reactor 20.

The reactor 20 is equipped with an external neutralisation loop 28 comprising a pump 25.

As in the first embodiment, the heat given off by the neutralisation makes possible an increase in the temperature of the solution until, at the most, the boiling point of the solution at the operating pressure is reached.

In order to condense the water thus evaporated, a condenser 23 is provided on the reactor 20.

The solution produced in the reactor 20 is directed (stream 24) to storage tanks (not represented).

The examples below illustrate more clearly the process of the invention and the characteristics and advantages of the latter.

EXAMPLES

Example 1

Production of a 52% by Weight Aqueous Solution of 66/6T 66/34 (Molar Proportion) Salt According to the Batchwise Process Preparation of the Solution (A')

An aqueous solution of terephthalic acid and of hexamethylenediamine is prepared by adding terephthalic acid (11.2 kg) to a liquid, the temperature of which is equal to 80° C., the latter being obtained by addition of hexamethylenediamine (18.2 kg of a 90% by weight aqueous solution) and of demineralised water (27.4 kg) to the reactor 5; this reactor comprises a heel of 22 kg of an aqueous solution of terephthalic acid, of adipic acid (in the molar proportion 34/66) and of hexamethylenediamine exhibiting a diacids/diamine molar ratio=1.017 at a temperature of 103° C. and a concentration by weight of dissolved entities of approximately 52%.

Advantageously, this solution heel is a small portion of the solution (A) obtained in the reactor 5 in a previous manufacturing operation.

The time for addition of the terephthalic acid is of the order of 4 minutes and its salification with hexamethylenediamine results in a rise in temperature of the medium. The reactor is provided with a mechanical stirrer. The dissolution of the terephthalic acid is obtained at the end of one minute after the end of introduction of the terephthalic acid. The aqueous solution obtained exhibits a concentration of dissolved entities of 49.5% by weight and the final temperature of the solution is 95° C.

Preparation of the Solution (B")

An aqueous solution of adipic acid and of hexamethylenediamine is prepared by simultaneously adding powdered adipic acid (18.8 kg) and hexamethylenediamine (6.7 kg of a 90% by weight aqueous solution at a temperature of 45° C.) to the thermally insulated reactor 1 comprising an aqueous solution obtained by addition of water (18 kg) to the heel of 14 kg of aqueous solution of adipic acid and of hexamethylenediamine exhibiting an AA/HMD molar ratio=2.5 at a temperature of 63° C. and a concentration by weight of dissolved entities of 57%.

Advantageously, this solution heel is a small portion of the solution (B") obtained in the reactor 1 in a previous manufacturing operation. The reactor is equipped with a mechanical stirrer. At the end of the preparation, the dissolved entities (57% by weight) consist of 75.6% by weight of adipic acid and 24.4% by weight of hexamethylenediamine. The final temperature of the solution is 63° C.

Preparation of the Solution (A)

43.6 kg (i.e., approximately 75.7%) of the solution (B") prepared above are then transferred into reactor 5 of FIG. 1, which is thermally insulated and equipped with a condenser 8. The diacids/diamine ratio of the solution obtained is close to stoichiometry (diacids/HMD molar ratio=1.017).

The energy or heat given off by the neutralisation reaction brings about the rise in the temperature of the medium up to the boiling point, namely approximately 103° C. in the example described. The vapours produced are condensed in the condenser 8 and form a total reflux into the reactor 5. The energy removed by the condensation of the vapours corresponds to the excess energy of neutralisation.

The concentration and the pH of the solution are subsequently adjusted by addition of 0.34 kg of a 90% by weight aqueous HMD solution at a temperature of 45° C., after transfer of a portion of the solution (100 kg) into a third reactor 10. At the end of this stage, the solution is an aqueous solution comprising 52% by weight of 66/6T salt with a diacids/HMD molar ratio equal to 1.003 and a pH equal to 7.20. The pH is measured at 40° C. on a sample of the solution diluted with water in order to obtain a concentration of dissolved entities equal to 100 g/l.

The solution obtained is subsequently stored in a tank 12 illustrated in FIG. 1.

Example 2

Production of a 52% by Weight Aqueous Solution of 66/6T 66/34 (Molar Proportion) Salt According to the Batchwise Process Preparation of the Solution (A')

An aqueous solution of terephthalic acid and of hexamethylenediamine is prepared by adding terephthalic acid (11.2 kg) to a liquid, the temperature of which is equal to 80° C., the latter being obtained by addition of hexamethylenediamine (24.9 kg of a 90% by weight aqueous solution) and of demineralised water (27.4 kg) to the reactor 5; this reactor comprises a heel of 22 kg of an aqueous solution of terephthalic acid, of adipic acid (in the molar proportion 34/66) and of hexamethylenediamine exhibiting a diacids/diamine molar ratio=1.017 at a temperature of 103° C. and a concentration by weight of dissolved entities of approximately 52%.

Advantageously, this solution heel is a small portion of the solution (A) obtained in the reactor 5 in a previous manufacturing operation.

The time for addition of the terephthalic acid is of the order of 4 minutes and its salification with hexamethylenediamine results in a rise in temperature of the medium. The reactor is provided with a mechanical stirrer. The dissolution of the terephthalic acid is obtained at the end of two minutes after the end of introduction of the terephthalic acid. The aqueous solution obtained exhibits a concentration of dissolved entities of 52.7% by weight and the final temperature of the solution is 96° C.

Preparation of the Slurry (B")

An aqueous slurry of adipic acid is prepared by adding powdered adipic acid (18.8 kg) to the reactor 1, which is thermally insulated and maintained at 70° C. by heating, the reactor comprising an aqueous slurry obtained by addition of water (18 kg) to a heel of 14 kg of aqueous slurry of adipic acid at a temperature of 70° C. and a concentration by weight of adipic acid (solid+dissolved) of 51%.

Advantageously, this slurry heel is a small portion of the slurry (B") obtained in the reactor 1 in a previous manufacturing operation. The reactor is equipped with a mechanical stirrer. At the end of the preparation, the aqueous slurry exhibits a concentration of adipic acid (solid+dissolved) of 51% by weight. The final temperature of the slurry is 70° C.

Preparation of the Solution (A)

36.8 kg (i.e., approximately 72.4%) of the slurry (B") prepared above are then transferred into reactor 5 of FIG. 1, which is thermally insulated and equipped with a condenser 8. The diacids/diamine ratio of the solution obtained is close to stoichiometry (diacids/HMD molar ratio=1.017).

The energy or heat given off by the neutralisation reaction brings about the rise in the temperature of the medium up to the boiling point, namely approximately 103° C. in the example described. The vapours produced are condensed in the condenser 8 and form a total reflux into the reactor 5. The energy removed by the condensation of the vapours corresponds to the excess energy of neutralisation.

The concentration and the pH of the solution are subsequently adjusted by addition of 0.34 kg of a 90% by weight aqueous HMD solution at a temperature of 45° C., after transfer of a portion of the solution (100 kg) into a third reactor 10. At the end of this stage, the solution is an aqueous solution comprising 52% by weight of 66/6T salt with a diacids/HMD molar ratio equal to 1.003 and a pH equal to 7.20. The pH is measured at 40° C. on a sample of the solution diluted with water in order to obtain a concentration of dissolved entities equal to 100 g/l.

The solution obtained is subsequently stored in a tank 12 illustrated in FIG. 1.

Example 3

Production of a 52% by Weight Aqueous Solution of 66/6T 56/44 (Molar Proportion) Salt According to the Batchwise Process Preparation of the Solution (A')

An aqueous solution of terephthalic acid and of hexamethylenediamine is prepared by adding terephthalic acid (14.3 kg) to a liquid, the temperature of which is equal to 80° C., the latter being obtained by addition of hexamethylenediamine (19.1 kg of a 90% by weight aqueous solution) and of demineralised water (30.4 kg) to the reactor 5, the latter comprising a heel of 22 kg of an aqueous solution of terephthalic acid, of adipic acid (in the molar proportion 44/56) and of hexamethylenediamine exhibiting a diacids/diamine molar ratio=1.017 at a temperature of 103° C. and a concentration by weight of dissolved entities of approximately 52%.

Advantageously, this solution heel is a small portion of the solution (A) obtained in the reactor 5 in a previous manufacturing operation.

The time for addition of the terephthalic acid is of the order of 4 minutes and its salification with hexamethylenediamine results in a rise in temperature of the medium. The reactor is provided with a mechanical stirrer. The dissolution of the terephthalic acid is obtained at the end of three minutes after the end of introduction of the terephthalic acid. The aqueous solution obtained exhibits a concentration of dissolved entities of 50% by weight and the final temperature of the solution is 95° C.

Preparation of the Solution (B")

An aqueous solution of adipic acid and of hexamethylenediamine is prepared by simultaneously adding powdered adipic acid (15.9 kg) and hexamethylenediamine (5.7 kg of a 90% by weight aqueous solution at a temperature of 45° C.) to the thermally insulated reactor 1 comprising an aqueous solution obtained by addition of water (15.1 kg) to the heel of 14 kg of aqueous solution of adipic acid and of hexamethylenediamine exhibiting an AA/HMD molar ratio=2.5 at a temperature of 63° C. and a concentration by weight of dissolved entities of 57%.

Advantageously, this solution heel is a small portion of the solution (B") obtained in the reactor 1 in a previous manufacturing operation. The reactor is equipped with a mechanical stirrer. At the end of the preparation, the dissolved entities (57% by weight) consist of 75.6% by weight of adipic acid and 24.4% by weight of hexamethylenediamine. The final temperature of the solution is 63° C.

Preparation of the Solution (A)

36.7 kg (i.e., approximately 72.4%) of the solution (B") prepared above are then transferred into reactor 5 of FIG. 1, which is thermally insulated and equipped with a condenser 8. The diacids/diamine ratio of the solution obtained is close to stoichiometry (diacids/HMD molar ratio=1.017).

The energy or heat given off by the neutralisation reaction brings about the rise in the temperature of the medium up to the boiling point, namely approximately 103° C. in the example described. The vapours produced are condensed in the condenser 8 and form a total reflux into the reactor 5. The energy removed by the condensation of the vapours corresponds to the excess energy of neutralisation.

The concentration and the pH of the solution are subsequently adjusted by addition of 0.34 kg of a 90% by weight aqueous HMD solution at a temperature of 45° C., after transfer of a portion of the solution (100 kg) into a third reactor 10. At the end of this stage, the solution is an aqueous solution comprising 52% by weight of 66/6T salt with a diacids/HMD molar ratio equal to 1.003.

The solution obtained is subsequently stored in a tank 12 illustrated in FIG. 1.

Example 4

Production of a 52% by Weight Aqueous Solution of 66/6T 66/34 (Molar Proportion) Salt According to the Batchwise Process Preparation of the Solution (A')

An aqueous solution of terephthalic acid and of hexamethylenediamine is prepared by adding terephthalic acid (11.2 kg) to a liquid, the temperature of which is equal to 80° C., the latter being obtained by addition of hexamethylenediamine (18.2 kg of a 90% by weight aqueous solution) and of demineralised water (27.4 kg) to the reactor 5.

The time for addition of the terephthalic acid is of the order of 4 minutes and its salification with hexamethylenediamine results in a rise in temperature of the medium. The reactor is provided with a mechanical stirrer. The dissolution of the terephthalic acid is obtained at the end of one minute after the end of introduction of the terephthalic acid. The aqueous solution obtained exhibits a concentration of dissolved entities of 48.5% by weight and the final temperature of the solution is 95° C.

Example 5 (Comparative)

Production of a 52% by Weight Aqueous Solution of 66/6T 66/34 (Molar Proportion) Salt According to the Batchwise Process Preparation of the Solution (A')

An aqueous solution of terephthalic acid and of hexamethylenediamine is prepared by adding terephthalic acid (11.2 kg) to a liquid, the temperature of which is equal to 50° C., the latter being obtained by addition of hexamethylenediamine (18.2 kg of a 90% by weight aqueous solution) and of demineralised water (27.4 kg), to the reactor 5.

The addition time for the terephthalic acid is of the order of 4 minutes and its salification with the hexamethylenediamine results in a very slight rise in temperature of the medium. The reactor is equipped with a mechanical stirrer.

The addition of the terephthalic acid results in the formation of large agglomerates, the dissolution of which is not obtained at the end of several hours (while maintaining the temperature at 50° C.).

This method of preparation does not make it possible to obtain a homogeneous solution (A'), in comparison with the method of preparation according to Example 4 of the invention, for example.

This method of preparation is not suitable for the preparation of a homogeneous solution.

The invention claimed is:

1. A process for manufacturing an aqueous solution comprising salts of diacids and at least one diamine, the process comprising:
   producing an aqueous solution (A') of diamine(s) and diacid(s) having a diacid/diamine molar ratio of less than 1, by feeding into a reactor (a) a liquid comprising water and diamine at a temperature from 55° C. to 95° C., (b) a stream (B') comprising an aliphatic or cycloaliphatic diacid comprising a number of carbon atoms of greater than 10 or an aromatic diacid, optionally (c) a stream comprising diamine, and optionally (d) a stream comprising water; wherein the flow rates of the feed stream or streams are controlled to always have a temperature of the solution in the reactor less than the boiling point of the solution under operating pressure; and the amounts of the water and diamine in the liquid and flow rates of the feed streams being controlled in order to always have a diacid(s)/diamine(s) molar ratio of less than 1;
   mixing the aqueous solution (A') resulting from the first stage with a stream (B") comprising at least one diacid, the diacid being an aliphatic or cycloaliphatic diacid comprising a number of carbon atoms of less than or equal to 10, and optionally supplementary water and/or supplementary diamine; and obtaining an aqueous solution (resulting from the mixing of (A') and (B")) having a diacids/diamine(s) molar ratio of between 0.9 and 1.1;
   bringing the solution to a temperature at most equal to the boiling point of the solution at operating pressure by at least a release of heat of reaction between the diamine(s) and the diacids; and
   obtaining an aqueous solution (A) comprising salts of diacids and diamine(s) having a concentration by weight of salt of between 40 and 70%.

2. The process according to claim 1, wherein the reactor is maintained under an atmosphere devoid of oxygen.

3. The process according to claim 1, wherein the diamine of the solution (A') and of the stream (B") is hexamethylenediamine.

4. The process according to claim 1, wherein the diacid of the stream (B') is terephthalic acid.

5. The process according to claim 1, wherein the diacid of the stream (B") is adipic acid.

6. The process according to claim 1, wherein the solution (A) exhibits a molar proportion of terephthalic acid, with respect to the diacids, of between 5% and 80%.

7. The process according to claim 1, wherein the liquid comprises all the water and diamine of the solution (A').

8. The process according to claim 1, wherein the stream (B") is an aqueous solution of diacid and of diamine with a diacid/diamine molar ratio of between 1.5 and 5 and a concentration in the water of the dissolved entities of between 40% and 75% by weight.

9. The process according to claim 1, wherein the diacid/diamine molar ratio in the aqueous solution (A') is less than or equal to 0.9.

10. The process according to claim 1, wherein the liquid in the reactor in which aqueous solution (A') is produced is at a temperature of from 60° C. to 90° C.

11. The process according to claim 1, wherein the aqueous solution (resulting from the mixing of (A') and (B')) has a molar ratio from 0.98 to 1.02.

12. The process according to claim 6, wherein the solution (A) has a molar proportion of terephthalic acid, with respect to the diacids, of between 20% and 50%.

13. The process according to claim 8, wherein the concentration in the water of the dissolved entities is between 45% and 65% by weight.

* * * * *